United States Patent
Hsieh et al.

(10) Patent No.: US 7,050,616 B2
(45) Date of Patent: May 23, 2006

(54) DATA TRANSMISSION SCHEME AND SYSTEM FOR IMAGE RECONSTRUCTION

(75) Inventors: Jiang Hsieh, Brookfield, WI (US); Phil E. Pearson, Jr., Hartland, WI (US); Dennis Harry Pritzkow, Pewaukee, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 761 days.

(21) Appl. No.: 10/113,156

(22) Filed: Apr. 1, 2002

(65) Prior Publication Data

US 2003/0185427 A1 Oct. 2, 2003

(51) Int. Cl.
*G06K 9/00* (2006.01)

(52) U.S. Cl. .......................... 382/131; 378/4
(58) Field of Classification Search ................ 382/128, 382/130–131, 300; 378/4, 18–19
See application file for complete search history.

(56) References Cited

U.S. PATENT DOCUMENTS

| | | | | |
|---|---|---|---|---|
| 5,243,664 A | * | 9/1993 | Tuy | ............................. 382/130 |
| 5,680,426 A | | 10/1997 | Ching-Ming | |
| 5,680,427 A | * | 10/1997 | Dobbs et al. | ................. 378/19 |
| 5,745,542 A | * | 4/1998 | Gordon et al. | ................. 378/4 |
| 6,115,445 A | | 9/2000 | Lai | |
| 6,148,057 A | * | 11/2000 | Urchuk et al. | ................ 378/18 |
| 6,212,256 B1 | | 4/2001 | Miesbauer et al. | |
| 6,307,908 B1 | * | 10/2001 | Hu | ............................... 378/4 |

FOREIGN PATENT DOCUMENTS

EP 0 446 033 A2 9/1991

OTHER PUBLICATIONS

International Search Report, dated Jul. 2, 2003, Application No. EP 03 25 1940, 3 pages.
Jiang Hsieh: "Image Artifacts, Causes, and Correction," Medical CT and Ultrasound: Current Technology and Applications, American Association of Physicists in Medicine, 1995, pp. 487-518.

* cited by examiner

*Primary Examiner*—Jose L. Couso
*Assistant Examiner*—Tom Y. Lu
(74) *Attorney, Agent, or Firm*—Carl B. Horton, Esq.; Armstrong Teasdale LLP

(57) ABSTRACT

A method for transmitting data in a computed tomography (CT) system includes detecting an error in at least one of a transmitted data sample in the CT system and a data sample to be transmitted in the CT system. The method also includes replacing the erroneous data sample with an error with interpolated data from neighboring data samples.

29 Claims, 3 Drawing Sheets

DATA TRANSMISSION SCHEME AND SYSTEM FOR IMAGE RECONSTRUCTION

BACKGROUND OF THE INVENTION

This invention relates to computed tomographic (CT) imaging, and more particularly to methods and apparatus for error correction in CT imaging systems.

Current CT designs are approaching rotational speeds of about 0.25 seconds, and slices per rotation are approaching 16 slices and beyond, resulting in an increase in raw data requirements across a slip ring. At least one known correction scheme uses Forward Error Correction codes (FEC). However, FEC coding consumes an appreciable amount of the bandwidth available across large bore slip rings. Therefore, total data rate requirements (including the FEC coding overhead) across the CT rotating interface will soon break the 100 Mbytes/sec barrier. Reliable, cost-effective commercial versions of large-bore slip rings do not have data bandwidths above 100 Mbytes/sec. Therefore known FEC correction schemes are becoming inadequate as raw data rate requirements increase.

BRIEF DESCRIPTION OF THE INVENTION

In one aspect, a method for transmitting data in a computed tomography (CT) system is provided. The method includes detecting an error in at least one of a transmitted data sample in the CT system and a data sample to be transmitted in the CT system. The method also includes replacing the erroneous data sample with an error with interpolated data from neighboring data samples.

In another aspect, a computer is programmed to detect an error in at least one of a transmitted data sample in a CT system and a data sample to be transmitted in the CT system, and replace the erroneous data sample with an error with interpolated data from neighboring data samples.

In yet another aspect, a computed tomographic (CT) imaging system for reconstructing an image of an object is provided. The imaging system includes a detector array, at least one radiation source; and a computer coupled to the detector array and the radiation source. The computer is configured to detect an error in at least one of a data sample transmitted within in the CT system and a data sample to be transmitted within the CT system and replace the erroneous data sample with an error with interpolated data from neighboring data samples.

DETAILED DESCRIPTION OF THE INVENTION

Figure 1:
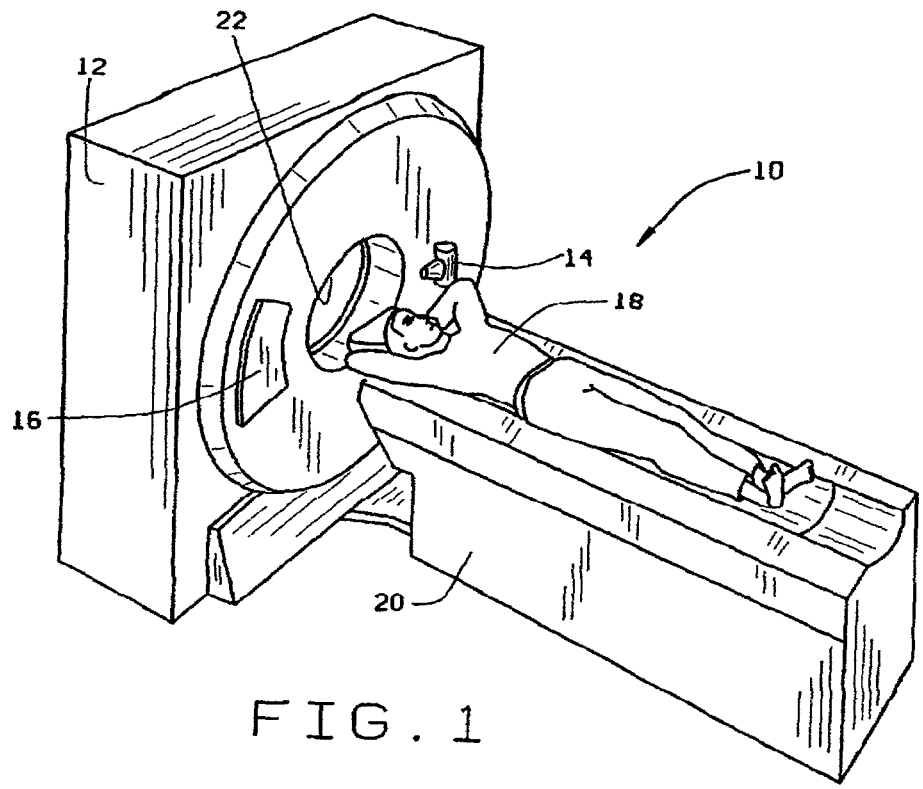
FIG. 1 is a pictorial view of a CT imaging system.

In some CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated beam radiation received at the detector array is dependent upon the attenuation of an x-ray beam by the object. Each detector element of the array produces a separate electrical signal that is a measurement of the beam attenuation at the detector location. The attenuation measurements from all the detectors are acquired separately to produce a transmission profile.

In third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display or film.

To reduce the total scan time, a "helical" scan may be performed. To perform a "helical" scan, the patient is moved while the data for the prescribed number of slices is acquired. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered back projection process, the data is weighted according to a helical weighing factor, which is a function of both the gantry angle and detector angle. The helical weighting algorithms also scale the data according to a scaling factor, which is a function of the distance between the x-ray source and the reconstruction plane. The weighted and scaled data is then processed to generate CT numbers and to construct an image that corresponds to a two dimensional slice taken through the object. Alternatively, interpolation can be performed on the collected projection data to produce a set of projection corresponds to the reconstruction plane. Filtered backprojection method is then used to construct an image that corresponds to a two-dimensional slice taken through the object. Of course, other helical reconstruction algorithms can also be used.

Referring now specifically to FIG. 1, a computed tomography (CT) imaging system 10 is shown as including a gantry 12 representative of a "third generation" CT scanner. Gantry 12 has an x-ray source 14 that projects a beam of x-rays toward a detector array 16 on the opposite side of gantry 12. Detector array 16 is formed by a plurality of detector modules which together sense the projected x-rays that pass through an object 18 such as, but not limited to, a medical patient 18. Each detector module produces an electrical signal that represents the intensity of an impinging x-ray beam and hence the attenuation of the beam as it passes through patient 18.

During a scan to acquire x-ray projection data, gantry 12 and the components mounted thereon rotate about a center of rotation. A motorized table 20 positions patient 18 relative to gantry 12. Particularly, table 20 moves portions of patient 18 through a gantry opening 22 during a scan.

Figure 2:
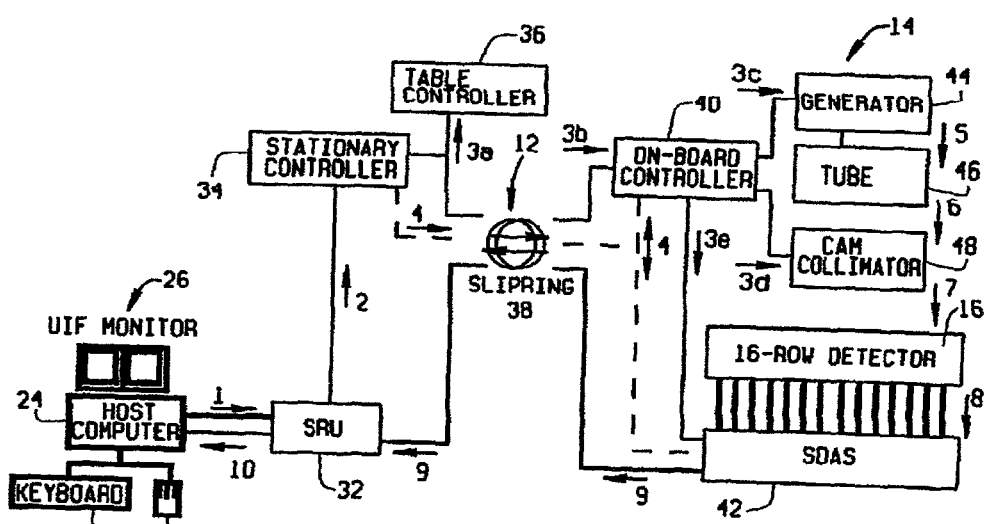
FIG. 2 is a block schematic diagram of the system illustrated in FIG. 1.

FIG. 2 is a block schematic diagram of the system illustrated in FIG. 1. As shown in FIG. 2, system 10 includes a host computer 24 coupled to a monitor (user interface) 26 for displaying images and messages to an operator. Computer 24 also is coupled to a keyboard 28 and an input device 30 such as a mouse 30 to enable the operator to input information and commands to computer 24. Computer 24 is coupled to a scan and reconstruction control unit (SRU) 32. SRU 32 also includes image generation controls. In one specific embodiment, SRU 32 includes a SGI PCI-based central processing unit which operates on an IRIX operating system. SRU 32 also includes an interface processor for interfacing with the data acquisition system (described below), and a scan data correction digital signal processing board for performing preprocessing, which is known in the art. SRU 32 further includes an image generator for filtered backprojection and postprocessing operations, as is known in the art.

A stationary controller 34 is connected to SRU 32, and controller 34 is coupled to a table controller 36. Stationary controller 34 also is connected, through a slipring 38, to an on-board controller 40 and a scalable data acquisition system (SDAS) 42. Slipring 38 enables contactless transmission of signals across the slipring boundary and supports the necessary bandwidth for transmission of data and commands across the boundary. SDAS 42 samples and acquires the data from detector 16 and converts the sampled analog signals to digital signals. SDAS 42, in one specific embodiment, includes forty eight interchangeable converter cards to support four row data acquisition. For two row data acquisition, twenty four cards could be used. In one specific embodiment, there are sixty four input channels per converter card and 1408 Hz sampling can be performed. SDAS 42 also includes a front-end pre-amplifier for amplifying the signals. In one embodiment, SDAS 42 is not scalable and is sometimes referred to herein as data acquisition system (DAS) 42.

On-board controller 40 controls operation of x-ray source 14 and operation of SDAS 42. X-ray source 14 includes a high voltage generator 44 coupled to an x-ray tube 46. Tube 46 may, for example, be the tube known in the art is the Gemini-1 tube and currently utilized in at least some CT system commercially available from General Electric Company, Milwaukee, Wis., 53201. Beams projected by X-ray tube 46 pass through a prepatient cam collimator 48 and impinge upon detector 16 (illustrated as a 16 row detector). Cam collimator 48 also is controlled by on-board controller 40. Outputs from detector 16 are supplied to DAS 42.

In FIG. 2, data flow is illustrated by bold lines, control flow is illustrated by normal lines, and real-time control flow is illustrated by dotted lines. The numeric identifiers associated with the flows are set forth below.

1: scan and reconstruction prescription from operator
2: scan prescription to "master" controller
3: scan parameters distributed
3a: table position
3b: rotating parameters
3c: kV and mA selections
3d: x-ray beam collimation and filter selections
3e: detector slice thickness and SDAS gain selections
4: real-time control signals during scanning
5: high voltage
6: un-collimated x-ray beam
7: collimated x-ray beam
8: analog scan data
9: digital scan data
10: patient images Rotation of gantry 12 and the operation of x-ray source 14 are governed by controller 34. On-board controller 40, under the control of stationary controller 34, provides power and timing signals to x-ray source 14. DAS 42 samples analog data from detector 16 and converts the data to digital signals for subsequent processing. SRU 32 receives sampled and digitized x-ray data from DAS 42 and performs high speed image reconstruction. The reconstructed image is applied as an input to computer 24 which stores the image in a mass storage device.

Computer 24 also receives commands and scanning parameters from an operator via keyboard 28 and mouse 30. Monitor 26 allows the operator to observe the reconstructed image and other data from computer 24. The operator supplied commands and parameters are used by computer 24 to provide control signals and information. In addition, controller 36 controls motorized table 20 to position patient 18 (shown in FIG. 1).

Generally, the above described CT system is operable to collect 1, 2 or more slices data. Axial and helical scans can be performed with the system, and cross section images of a scanned object can be processed, reconstructed, displayed and/or archived. Scalable axial image reconstruction and display refers, for example, to selectability of the image thickness, number of slices, and number of images to be displayed. Further, the system is not limited to practice with any one particular image reconstruction algorithm, and it is contemplated that many different reconstruction algorithms can be utilized. Exemplary algorithms are set forth in U.S. Pat. Nos. 5,469,487, 5,513,236, 5,541,970, 5,559,847, 5,606,585, and 5,828,719, all of which are assigned to the present assignee.

In one embodiment, computer 24 includes a device (not shown), for example, a floppy disk drive or CD-ROM drive, for reading instructions and/or data from a computer-readable medium (not shown), such as a floppy disk or CD-ROM. In another embodiment, computer 24 executes instructions stored in firmware (not shown). Computer 24 is programmed to perform functions described herein, but other programmable circuits can be likewise programmed. For example, in one embodiment, DAS 42 performs functions described herein. Accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits. Additionally, although described in a medical setting, it is contemplated that the benefits of the invention accrue to all CT systems including industrial CT systems such as, for example, but not limited to, a baggage scanning CT system typically used in a transportation center such as, for example, but not limited to, an airport or a rail station.

Figure 3:
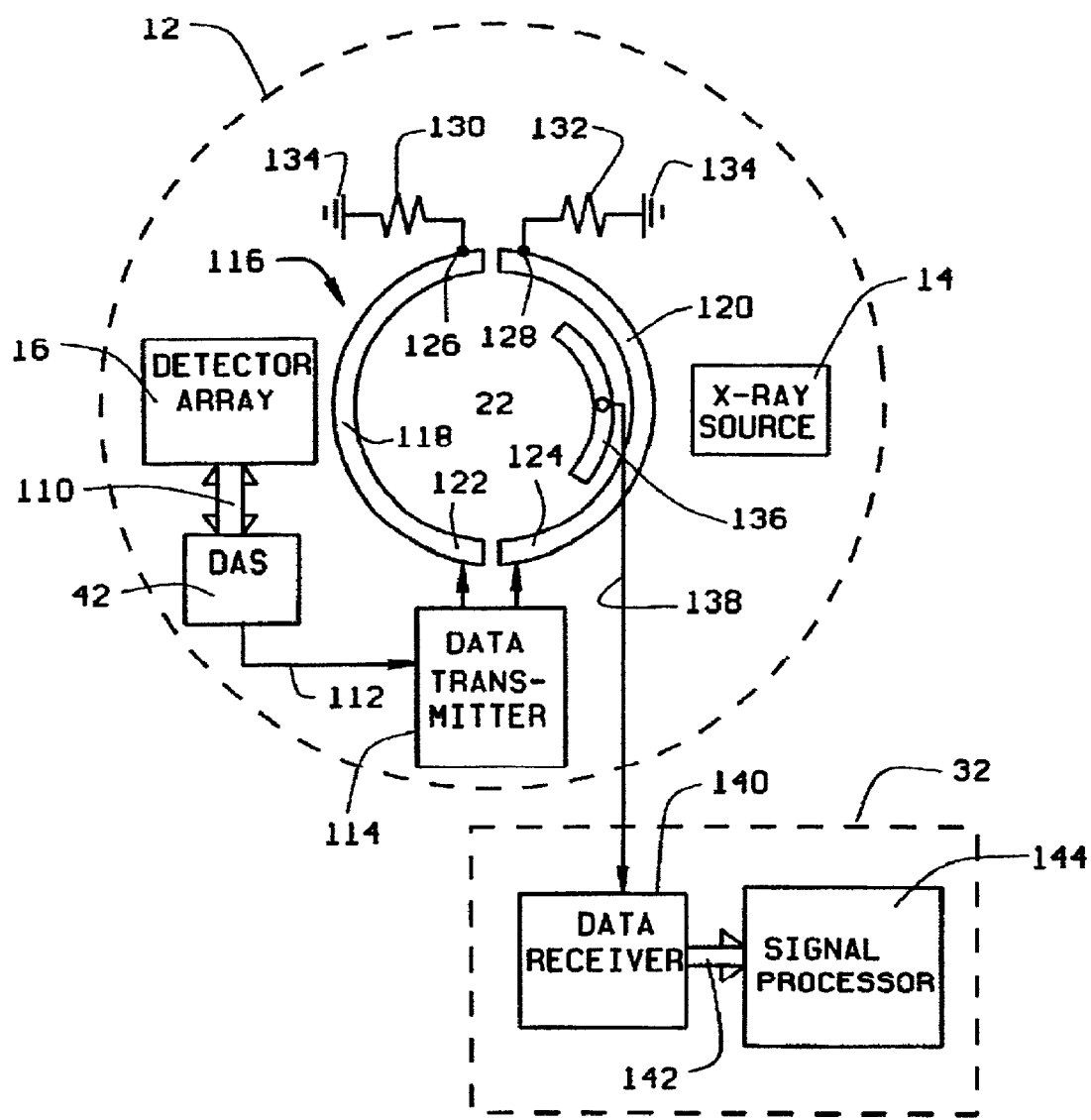
FIG. 3 illustrates generated images of a patient scan.

Referring now to FIG. 3, which is a simplified, figurative schematic block diagram of gantry 12. The signals from detector array 16 are provided through lines 110 to data acquisition system DAS 42, which converts each signal from an analog signal format into digital data, typically, two bytes having 16 bits. The digital data is provided on lines 112 to a data transmitter 114 disposed on gantry 12. Data transmitter 114 digitally encodes the data with an RF (radio frequency) pulse pattern, and the RF encoded signal is presented to an electromagnetic coupler, such as an RF slip ring 116 similar to the type disclosed in U.S. Pat. No. 5,530,424 to Harrison et al, which is assigned to the assignee of this application.

The slip ring configuration includes one or more transmission lines disposed on the rotating side of the interface; one coupler segment mounted on the relatively stationary side. Depending on the distance between the stationary coupler and the rotating transmission line, a number of transmission line segments may be required to ensure that the coupler is always in spatial proximity to at least one of the segments to receive the electromagnetic signal. In that case each segment has a length which is a fractional portion of the arc length of the gantry's rotational path. The segments are cascaded, end-to-end around the gantry's rotational axis, typically along the circumference of opening 22 such that the aggregate length provides a substantially 360 degree arc, i.e. a full rotation of the gantry.

Two transmission line segments 118, 120 are used and are mounted in a manner to provide adjacent positioning of first ends 122, 124 and second ends 126, 128 of transmission lines 118, 120, respectively. Contiguous placement of the ends of each of the transmission lines provides substantial continuity of the electromagnetic coupling along the full rotational path of the gantry.

Data transmitter 114 provides the encoded data to first ends 122, 124 of each of the transmission lines 118, 120. Second ends 126, 128 of each transmission line are connected through terminal impedance's 130, 132 to signal ground 134. A coupler element 136 positioned on the stationery frame in a manner to ensure physical proximity of the coupler to one and both of the transmission lines 118, 120 during gantry rotation. The encoded data is electromagnetically coupled through to coupler 136, as described in the '424 patent to Harrison et al.

On the stationery frame side, the coupled data signal is provided on a line 138 to SRU 32. The encoded data is received at a data signal receiver 140. Signal receiver 140 decodes the serial data and provides the decoded data through lines 142 to a signal processor 144. Signal processor 144 includes signal memory (not shown) for storing the program algorithms which govern the CT processing of the received data in response to operator commands. Signal processor 144 collates the decoded imaging data sets into a composite view associated with the particular angular position of the gantry.

Instead of utilizing known FEC coding, data transmitter and signal receiver 140 use a novel error-detection coding scheme. Once a transmission error is detected, a flag is set in the packet to inform the reconstruction algorithm. The reconstruction algorithm will isolate the channel that contains the error. This can be accomplished quite easily by taking the derivatives of the projection samples in γ, β, and detector row directions, as shown by the following equations:

$$d\gamma(\gamma, \beta, n) = \frac{\partial}{\partial \gamma} p(\gamma, \beta, n) \quad \text{Eq. 1}$$

$$d\beta(\gamma, \beta, n) = \frac{\partial}{\partial \beta} p(\gamma, \beta, n) \quad \text{Eq. 2}$$

$$dn(\gamma, \beta, n) = \frac{\partial}{\partial n} p(\gamma, \beta, n) \quad \text{Eq. 3}$$

where n represents detector row, γ is the detector channel angle, β is the projection view angle, and p(γ, β, n) represents the measured projection after pre-processing. First the samples within the packet that exhibit the highest magnitude in the differential signal are identified. Then either the "majority rule" (a measurement is identified by two out of three differential signals) is applied or a weighted average of all differential signals is applied to determine which projection sample contains error. Once the channel(s) location is identified, these channels are replaced by interpolated signals using their neighboring samples. For interpolation, either linear or higher order (e.g., Lagrange interpolation or cubic-spline interpolation) interpolation schemes can be utilized. Because the samples are dynamically compensated, multiple erroneous samples in the projection data set can be tolerated without aborting the scan. Therefore, a higher error rate can be tolerated for slip ring 116.

Figure 4:
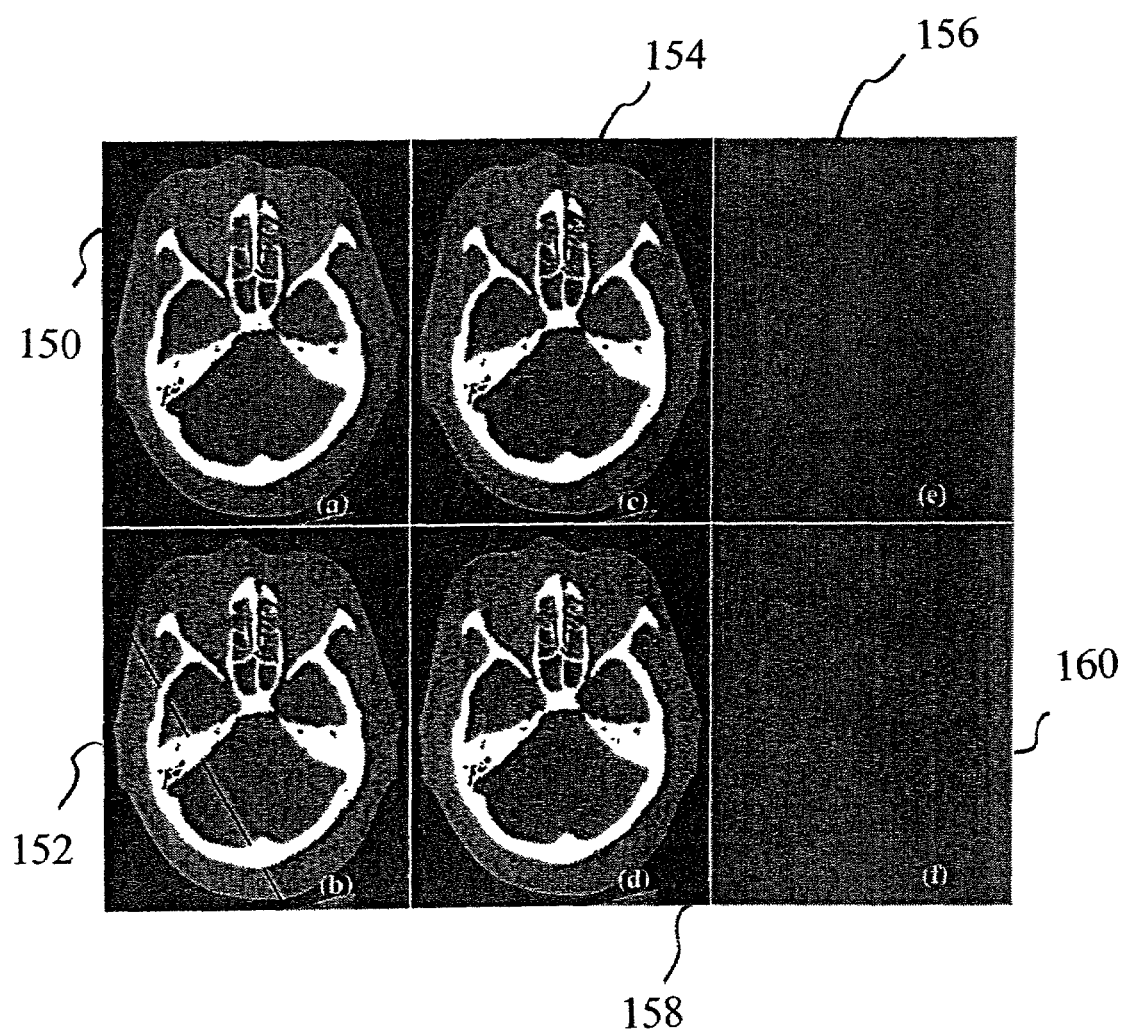
FIG. 4 illustrates a plurality of images of a patient scan corrected with masking.

FIG. 4 depicts experimental results of a human skull phantom. FIG. 4 includes a reconstructed image 150 without any error. This serves as a reference image. FIG. 4 also includes a simulated transmission error image 152 in which two adjacent samples are corrupted. A dark-bright streaking pattern can be clearly observed. Using the scheme presented above, the corrupted samples are replaced by linearly interpolated samples of their neighboring samples. The corrected image is shown in image 154. It is clear from the images that corrected image 154 and error-free image 150 are visually identical. The maximum CT number difference between the two images is 4 Hounsfield Units (HU). FIG. 4 also includes a difference image 156 illustrating the difference between images 150 and 154.

Alternatively, the entire view that contains the erroneous samples is replaced. There are two advantages of this approach. First, since the error flag is placed one per view (instead of one per packet), the amount of overhead is further reduced. Second, since the entire view is replaced, the error location identification as outlined previously does not need to be performed. The entire view is replaced by the interpolated view based on neighboring views. Similarly, either linear or high order interpolation schemes can be utilized. FIG. 4 also includes a corrected image 158 using linear interpolation of two adjacent views. The maximum CT number difference between the corrected image and the original is 12 HU. It is worth noting that the maximum difference can be further reduced by higher order interpolations. A difference image 160 between corrected image 158 and original image 150 is also shown in FIG. 4.

Alternatively, a single row in an erroneous view can be replaced. In this case, the error flag is placed one per row per view. The row can be replaced by interpolating projections across the neighboring rows of the same view, or by interpolating projections across views of the same row.

Alternatively, the combination of these sample replacements can be used. For example, if the number of errors per view falls below a pre-determined threshold, only the erroneous channels are replaced. If the number of errors per view exceeds a pre-determined threshold, the entire view or entire row is replaced.

Additionally, the amount of overhead on data transmission can be further reduced by using the error-isolation algorithm presented in Eqs. 1–3 exclusively (instead of the error flag per packet or view). Once an error sample is identified, the erroneous sample is replaced by the interpolated values of its neighbors prior to transmission. Because the error rate is typically quite low, a large number of errors are not present in the projection samples that formulate a single image. Using phantom and clinical experiments, a much higher error rate threshold can be set. This will allow the scan and image generation to continue, despite the presence of erroneous samples.

Additionally, using error detection allows for a monitoring mechanism for the "health" of the slip ring and/or other components of the scanner. For example, a plot or other trend-analysis of the error rate and error pattern over time is made to identify potential problems of slip ring 116. Examination of the error rate trend analysis facilitates the prediction of a failure of the slip ring before a failure actually takes place. This allows a service engineer to proactively replace or repair the component and avoid scanner downtime. Another example is the correlation of the detected error with other component failure on the scanner. For example, one can correlate the detected transmission error against tube-spit error detected on the scanner. If majority of the transmission failure coincides with the tube-spit, a tube replacement should be schedule instead of a slip-ring replacement.

Although the above is described in the context of slip ring induced errors, it should be understood that the same principle can be applied to other transmission errors in a CT system. For example, the above error detection and correction scheme compensates for errors in an Ethernet data bus, a data storage device or data storage media, as well as other non-slip ring induced errors.

Although particular embodiments of the invention have been described and illustrated in detail, it is to be clearly understood that the same is intended by way of illustration and example only and is not to be taken by way of limitation. In addition, the CT system described herein is a "third generation" system in which both the x-ray source and detector rotate with the gantry. However, many other CT systems including "fourth generation" systems wherein the detector is a full-ring stationary detector and only the x-ray source rotates with the gantry may be used. While the invention has been described in terms of various specific embodiments, those skilled in the art will recognize that the invention can be practiced with modification within the spirit and scope of the claims.

What is claimed is:

1. A method for transmitting data in a computed tomography (CT) system, said method comprising:
   detecting a data transmission error in at least one of a transmitted data sample in the CT system and a data sample to be transmitted in the CT system; and
   replacing the erroneous data sample with interpolated data from neighboring data samples including replacing only erroneous channels when a number of errors per view falls below a pre-determined threshold and replacing at least one of an entire view and an entire row when the number of errors per view exceeds a pre-determined threshold.

2. A method in accordance with claim 1 wherein said replacing the data further comprises replacing the erroneous data sample with linearly interpolated data from neighboring data samples.

3. A method in accordance with claim 1 further comprising performing a trend analysis of the error detection.

4. A method in accordance with claim 1 further comprising correlating transmission error with other component failure.

5. A method in accordance with claim 1 wherein said replacing the erroneous data sample with interpolated data from neighboring data samples comprises:
   locating the data sample; and
   replacing the erroneous data sample with interpolated data from neighboring data samples on a sample by sample basis.

6. A method in accordance with claim 1 wherein said replacing the erroneous data sample with interpolated data from neighboring data samples comprises replacing the erroneous data sample with interpolated data from neighboring data samples on a view by view basis.

7. A method in accordance with claim 1 wherein said replacing the erroneous data sample with interpolated data from neighboring data samples comprises replacing the erroneous data sample with interpolated data from neighboring data samples on a view by view basis prior to transmission of the data.

8. A method in accordance with claim 4 wherein said performing a trend analysis to predict a failure comprises performing a trend analysis to predict a failure in at least one of a slip ring, an Ethernet data bus and at least one of a data storage device and data storage media.

9. A method in accordance with claim 1 wherein said replacing the data further comprises replacing the data sample with an error with higher order interpolated data from neighboring data samples.

10. A method in accordance with claim 1 wherein said replacing the erroneous data sample with interpolated data from neighboring data samples comprises replacing the erroneous data sample with interpolated data from neighboring data samples on a row by row basis prior to transmission of the data.

11. A computer comprising a computer program embodied on a computer readable medium, said program configured to instruct the computer to:
    detect a data transmission error in at least one of a transmitted data sample in a CT system and a data sample to be transmitted in the CT system; and
    replace the erroneous data sample with an error with interpolated data from neighboring data samples including replace only erroneous channels when a number of errors per view falls below a pre-determined threshold and replace at least one of an entire view and an entire row when the number of errors per view exceeds a pre-determined threshold.

12. A computer in accordance with claim 11 further programmed to replace the erroneous data sample with linearly interpolated data from neighboring data samples.

13. A computer in accordance with claim 12 further programmed to track incidents of error detection.

14. A computer in accordance with claim 12 further programmed to perform a trend analysis on the tracked data to predict a failure.

15. A computer in accordance with claim 12 further programmed to:
    locate the data sample; and
    replace the erroneous data sample with interpolated data from neighboring data samples on a sample by sample basis.

16. A computer in accordance with claim 12 further programmed to replace the erroneous data sample with interpolated data from neighboring data samples on a view by view basis.

17. A computer in accordance with claim 12 further programmed to replace the erroneous data sample with interpolated data from neighboring data samples on a view by view basis prior to transmission of the data.

18. A computer in accordance with claim 14 further programmed to perform a trend analysis to predict a failure in at least one of a slip ring, an Ethernet data bus and at least one of a data storage device and data storage media.

19. A computer in accordance with claim 12 further programmed to replace the data sample with an error with higher order interpolated data from neighboring data samples.

20. A computer in accordance with claim 11 further programmed to replace the erroneous data sample with interpolated data from neighboring data samples on a row by row basis prior to transmission of the data.

21. A computed tomographic (CT) imaging system for reconstructing an image of an object, said imaging system comprising:
   a detector array;
   at least one radiation source; and
   a computer coupled to said detector array and said radiation source, said computer configured to:
   detect a data transmission error in at least one of a data sample transmitted within in the CT system and a data sample to be transmitted within the CT system; and
   replace the erroneous data sample with an error with interpolated data from neighboring data samples including replace only erroneous channels when a number of errors per view falls below a pre-determined threshold and replace at least one of an entire view and an entire row when the number of errors per view exceeds a pre-determined threshold.

22. A CT system in accordance with claim 21 wherein said computer is further programmed to replace the erroneous data sample with linearly interpolated data from neighboring data samples.

23. A CT system in accordance with claim 21 wherein said computer is further programmed to track incidents of error detection.

24. A CT system in accordance with claim 23 wherein said computer is further programmed to perform a trend analysis on the tracked data to predict a failure.

25. A CT system in accordance with claim 24 wherein said computer is further programmed to:
   locate the data sample; and
   replace the erroneous data sample with interpolated data from neighboring data samples on a sample by sample basis.

26. A CT system in accordance with claim 25 wherein said computer is further programmed to replace the erroneous data sample with interpolated data from neighboring data samples on a view by view basis.

27. A CT system in accordance with claim 25 wherein said computer is further programmed to replace the erroneous data sample with interpolated data from neighboring data samples on a view by view basis prior to transmission of the data.

28. A CT system in accordance with claim 24 wherein said computer is further programmed to perform a trend analysis to predict a failure in at least one of a slip ring, an Ethernet data bus and at least one of a data storage device and data storage media.

29. A CT system in accordance with claim 21 wherein said computer is further programmed to replace the data sample with an error with higher order interpolated data from neighboring data samples.

* * * * *